United States Patent
Sandholm et al.

(10) Patent No.: US 9,770,217 B2
(45) Date of Patent: Sep. 26, 2017

(54) DENTAL VARIATION TRACKING AND PREDICTION

(71) Applicants: Dental Imaging Technologies Corporation, Hatfield, PA (US); PaloDEx Group OY, Tuusula (FI)

(72) Inventors: Joonas Erik Sandholm, Helsinki (FI); Matti Petri Jouhikainen, Jarvenpaa (FI); Robert Frank Dillon, Mt. Pleasant, SC (US)

(73) Assignees: Dental Imaging Technologies Corporation, Hatfield, PA (US); PaloDEx Group OY, Tuusula (FI)

( * ) Notice: Subject to any disclaimer, the term of this patent is extended or adjusted under 35 U.S.C. 154(b) by 159 days.

(21) Appl. No.: 14/610,226

(22) Filed: Jan. 30, 2015

(65) Prior Publication Data

US 2016/0220200 A1     Aug. 4, 2016

(51) Int. Cl.
*A61B 6/14* (2006.01)
*A61C 7/00* (2006.01)
(Continued)

(52) U.S. Cl.
CPC .............. *A61B 6/14* (2013.01); *A61B 5/0035* (2013.01); *A61B 5/0066* (2013.01);
(Continued)

(58) Field of Classification Search
CPC ....... A61B 6/14; A61B 5/0035; A61B 5/0066; A61B 5/0071; A61B 5/0086;
(Continued)

(56) References Cited

U.S. PATENT DOCUMENTS

| 4,764,012 A | * | 8/1988 | Ryden | G01B 9/021 356/457 |
| 4,941,164 A | * | 7/1990 | Schuller | A61B 6/14 378/162 |

(Continued)

FOREIGN PATENT DOCUMENTS

| EP | 0950228 A2 * | 10/1999 | A61B 1/24 |
| EP | 2238888 A1 * | 10/2010 | A61B 1/00147 |

(Continued)

OTHER PUBLICATIONS

European Search Report for Application No. 16153422 dated Jun. 7, 2016 (2 pages).

*Primary Examiner* — Manav Seth
(74) *Attorney, Agent, or Firm* — Michael Best & Friedrich LLP

(57) ABSTRACT

Systems and methods are presented for evaluating a dental condition. A first digital representation of at least a portion of an oral cavity of a first patient is compared to a second digital representation of the oral cavity of the same patient. The first digital representation is representative of the oral cavity of the first patient at a first time and the second digital representation is representative of the oral cavity of the first patient at a second, later time. At least one clinically-significant difference between the first digital representation and the second digital representation are automatically identified and the first digital representation is displayed in a way that highlights the at least one clinically significant difference.

23 Claims, 6 Drawing Sheets

(51) Int. Cl.
*A61C 9/00* (2006.01)
*A61B 5/00* (2006.01)
*A61B 5/01* (2006.01)
*A61B 5/05* (2006.01)
*A61B 6/03* (2006.01)
*A61B 6/00* (2006.01)
*A61B 8/08* (2006.01)

(52) U.S. Cl.
CPC .......... *A61B 5/0071* (2013.01); *A61B 5/0086* (2013.01); *A61B 5/0088* (2013.01); *A61B 5/015* (2013.01); *A61B 5/0507* (2013.01); *A61B 5/4547* (2013.01); *A61B 5/4848* (2013.01); *A61B 5/7246* (2013.01); *A61B 5/7275* (2013.01); *A61B 5/743* (2013.01); *A61B 5/748* (2013.01); *A61B 5/7425* (2013.01); *A61B 6/032* (2013.01); *A61B 6/466* (2013.01); *A61B 6/5205* (2013.01); *A61B 8/08* (2013.01); *A61C 7/002* (2013.01); *A61C 9/004* (2013.01); *A61C 9/0053* (2013.01)

(58) Field of Classification Search
CPC ..... A61B 5/0088; A61B 5/015; A61B 5/0507; A61B 5/4547; A61B 5/4848; A61B 5/7246; A61B 5/7275; A61B 5/7425; A61B 5/743; A61B 5/748; A61B 6/032; A61B 6/466; A61B 6/5205; A61B 8/08; A61C 7/002; A61C 9/004; A61C 9/0053
See application file for complete search history.

(56) References Cited

U.S. PATENT DOCUMENTS

| | | | | |
|---|---|---|---|---|
| 5,113,424 A | * | 5/1992 | Burdea | A61B 6/08 378/168 |
| 5,372,502 A | * | 12/1994 | Massen | G01B 11/24 433/215 |
| 5,562,448 A | * | 10/1996 | Mushabac | A61C 13/0004 433/215 |
| 6,190,042 B1 | * | 2/2001 | Dove | A61B 6/145 378/167 |
| 6,201,880 B1 | * | 3/2001 | Elbaum | A61B 1/24 348/66 |
| 6,402,707 B1 | * | 6/2002 | Ernst | A61B 5/1076 433/214 |
| 6,575,751 B1 | * | 6/2003 | Lehmann | C07K 14/705 433/223 |
| 8,354,222 B2 | * | 1/2013 | Lee | G01N 33/57419 356/301 |
| 8,520,918 B2 | * | 8/2013 | Wilson | A61B 5/0033 382/128 |
| 8,706,672 B2 | * | 4/2014 | Malfliet | A61C 19/04 264/16 |
| 8,768,036 B2 | * | 7/2014 | Caligor | A61B 6/14 382/132 |
| 8,792,695 B2 | * | 7/2014 | Wilson | A61B 5/0033 382/128 |
| 8,973,269 B2 | * | 3/2015 | Johnson | A61C 13/0004 264/16 |
| 9,089,388 B2 | * | 7/2015 | Zegarelli | A61C 13/0013 |
| 9,192,305 B2 | * | 11/2015 | Levin | A61B 5/0088 |
| 2002/0150859 A1 | * | 10/2002 | Imgrund | A61C 7/00 433/24 |
| 2002/0176619 A1 | * | 11/2002 | Love | G06K 9/00154 382/154 |
| 2006/0188065 A1 | * | 8/2006 | Razzano | A61B 6/145 378/98 |
| 2007/0140539 A1 | * | 6/2007 | Katsumata | A61B 1/0676 382/128 |
| 2008/0124681 A1 | | 5/2008 | Cha | |
| 2011/0070554 A1 | * | 3/2011 | Kopelman | A61B 5/0002 433/29 |
| 2011/0316978 A1 | | 12/2011 | Dillon et al. | |
| 2013/0172731 A1 | * | 7/2013 | Gole | A61B 5/0035 600/424 |
| 2014/0329194 A1 | * | 11/2014 | Sachdeva | A61C 7/002 433/24 |
| 2015/0118638 A1 | * | 4/2015 | Cowburn | A61C 9/0006 433/29 |
| 2015/0265372 A1 | * | 9/2015 | Kim | A61C 1/082 433/75 |
| 2015/0265374 A1 | * | 9/2015 | Masoud | A61C 7/002 382/128 |
| 2015/0272710 A1 | * | 10/2015 | Krischollek | A61C 9/004 703/1 |
| 2016/0302887 A1 | * | 10/2016 | Schiemann | A61C 7/002 |

FOREIGN PATENT DOCUMENTS

| | | | | |
|---|---|---|---|---|
| JP | 2013074929 A | * | 4/2013 | |
| KR | 20150006807 A | * | 1/2015 | |
| WO | WO 9829050 A2 | * | 7/1998 | .............. A61B 1/24 |
| WO | 2006065955 | | 6/2006 | |

* cited by examiner

DENTAL VARIATION TRACKING AND PREDICTION

BACKGROUND

Embodiments of the invention relate to systems and method for utilizing dental imaging modalities for screening, diagnostics, patient communication, manufacturing of treatment appliances, and monitoring treatment programs.

SUMMARY

In one embodiment, the invention provides a method of evaluating a dental condition. A first digital representation of at least a portion of an oral cavity of a first patient is compared to a second digital representation of at least a portion of the oral cavity of the same patient. The first digital representation is representative of the oral cavity of the first patient at a first time and the second digital representation is representative of the oral cavity of the first patient at a second, later time. At least one clinically-significant difference between the first digital representation and the second digital representation are automatically identified and the second digital representation is displayed in a way that highlights the at least one clinically-significant difference.

In some embodiments, the second digital representation is indicative of a current condition of the patient's oral cavity and the first digital representation is indicative of the condition of the patient's oral cavity at an earlier time (e.g., a previous office visit). In other embodiments, the first digital representation is indicative of the current condition of the patient's oral cavity and the second digital representation is a predictive representation of a future state of the patient's oral cavity. In this way, the system can demonstrate to the patient how ongoing treatment (or lack thereof) will likely affect the patient's oral health.

In still other embodiments, the first digital representation is indicative of a previous condition of the patient's oral cavity and the second digital representation is an estimated representation of the current condition of the patient's oral cavity. By comparing the digital representations, the system can provide an estimated, predicted view of a patient's oral cavity before an office visit to allow the dental professional to analyze and evaluate potential treatment plans before the patient arrives at the office.

In yet another embodiment, the invention provides a method of evaluating a dental condition. A first digital representation of at least a portion of an oral cavity of a first patient is compared to a second digital representation of at least a portion of the oral cavity of the same patient. The first digital representation is representative of the oral cavity of the first patient at a first time and the second digital representation is representative of the oral cavity of the first patient at a second, later time. At least one clinically-significant difference between the first digital representation and the second digital representation are automatically identified and the first digital representation is displayed in a way that highlights the at least one clinically-significant difference.

In another embodiment, the invention provides a method of evaluating a dental condition. A first digital representation of at least a portion of an oral cavity of a first patient is compared to a second digital representation of at least a portion of the oral cavity of the same patient. The first digital representation is representative of the oral cavity of the first patient at a first time and the second digital representation is representative of the oral cavity of the first patient at a second, later time. At least one clinically-significant difference between the first digital representation and the second digital representation are automatically identified and a combination of the first digital representation and the second digital representation is displayed in a way that highlights the at least one clinically-significant difference.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
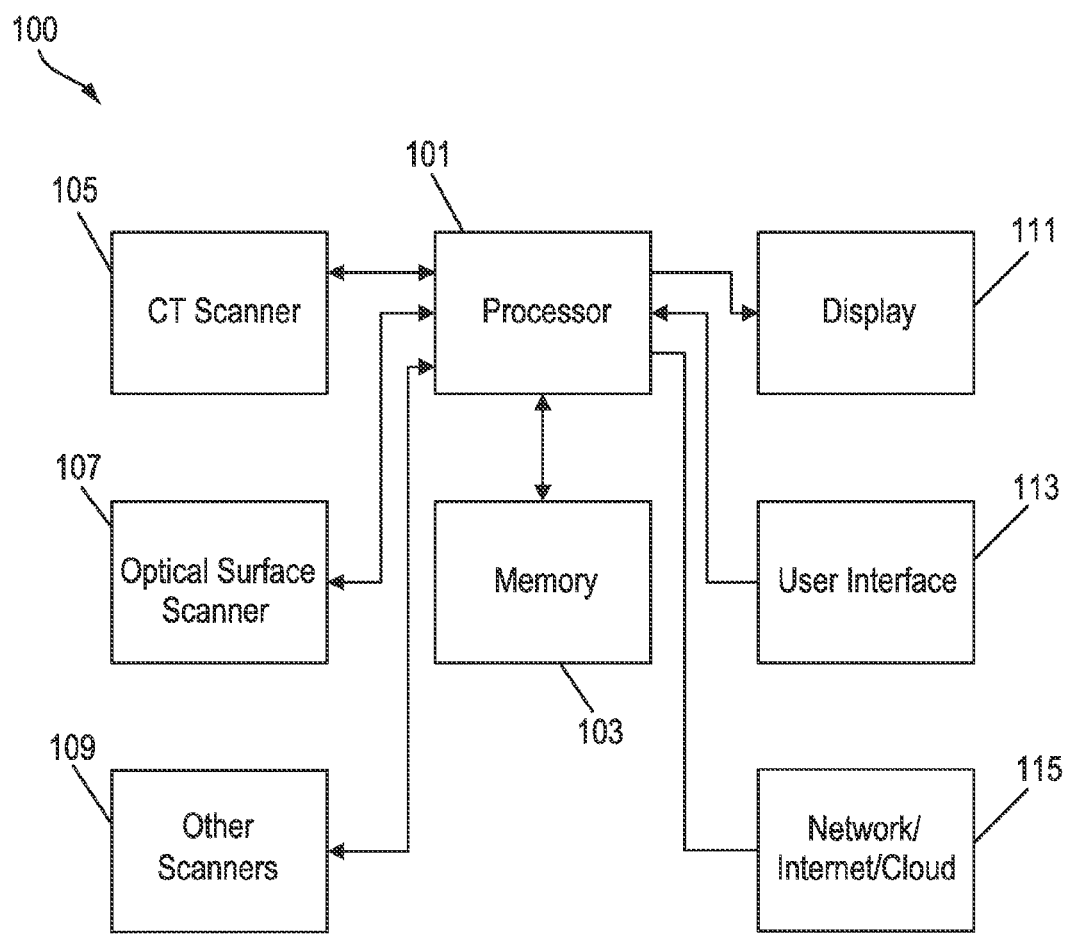
FIG. 1 is a block diagram of a system for monitoring and tracking dental variations.

FIG. 1 illustrates a system 100 for capturing, processing, analyzing, and comparing dental imaging scans. A processor 101 is coupled to a non-transitory computer-readable memory 103. The memory 103 can include, for example, one or more hard disks, flash memory modules, or cloud storage devices. The memory 103 stores instructions that are accessed and executed by the processor 101 to provide functionality, for example, as described in further detail below. The processor 101 is communicatively coupled to one or more imaging capture devices (e.g., a CT scanner 105, an optical surface scanner 107, and other types of imaging modality scanners or imaging devices 109, which may include, for example, an optical camera). Three-dimensional or two-dimensional digital renderings captured by the various scanning platforms and/or imaging devices are stored on the memory 103 for analysis and manipulation. Depending on the imaging modality, these digital renderings can include 2 or 3 dimensional geometrical data as well as other information including, for example, color, shade, and texture. The stored renderings are also accessible at later dates, for example, to provide the comparison functionality described below.

Digital renderings captured by the imaging platforms and stored on the memory 103 can be displayed on a display unit 111 (e.g., a high-definition video monitor). The system 100 also receives various input and instructions from a user through a user interface device 113 as described in further detail below. The system 100 is also capable of communicating with other systems through a network (e.g., a local-area or wide-area network) or the Internet 115. The system 100 thereby is able to access data and digital renderings stored on an external system and is also able to transmit locally stored images and data to external systems.

The system 100 is configured to perform various analysis and manipulation of dental imaging data captured by the connected dental scanning platforms. For example, as described further below, the system 100 is configured to scan a patient's oral cavity using the 3D optical scanner 107. In some constructions, the 3D optical scanner 107 uses an optical mechanism (e.g., lasers) to capture surface contour details and generates a 3D surface model of the oral cavity based on the geometric details. In other constructions, the 3D optical scanner 107 generates a photorealistic 3D digital surface model. The photorealistic 3D digital surface model may be generated by mapping color photographic data onto a 3D surface model. Some examples of techniques used to map photographic data onto a surface model are discussed in U.S. Patent Publication No. 2011/0316978, the entire contents of which are incorporated herein by reference. Photographic texture mapping on to three-dimensional models may also be accomplished by implementing a system based on software packages such as the Open GL Cube Map extension from NVIDIA Corporation.

In some constructions, the 3D optical scanner 107 also provides for detection and visual representation of caries and soft-tissue changes in the oral cavity. Both the upper and lower jaws can be scanned independently so that the system 100 can display the mouth in a "jaws open" positioning as well as displaying the 3D renderings in occlusion.

The system 100 is also designed to overlay multiple scans (i.e., stored 3D renderings) to automatically display changes. This overlaid display mechanism automatically provides for screening of possible problems, supporting diagnosis, and communicating status/changes with the patient. The system 100 is capable of demonstrating changes in tooth form (i.e., tooth wear, decay of enamel, chipping, loss of restorations, etc.) as well as changes in tooth position in relation to each other. Changes in tooth position may require orthodontic treatment and there are also other possible health conditions that impact tooth position. The system 100 also shows changes in tooth color indicative of staining (e.g., an opportunity for new whitening treatments), tooth vitality (teeth turn dark once they lose vitality), and calculus development.

The system 100 also detects and demonstrates changes in oral soft tissues. For example, the system 100 can show retraction of the gum line over time which may be indicative of periodontal disease or incorrect brushing technique. The system 100 can also detect and highlight changes in soft tissue shape indicative of swelling or other subgingival changes. Changes in color of various oral soft tissues (e.g., tongue, palate, cheeks, gingiva, etc.) are also detected and displayed to the user.

Various other constructions of the system are capable of capturing, tracking, and detecting other changes in a patient's oral cavity. For example, a fluorescence imaging system can be used to detect changes in the chemical structure of the teeth indicative of caries and demineralization. This chemical analysis is also displayed as a three-dimensional rendering by mapping the chemical scan data to another three-dimensional model captured, for example, by the CT or optical scanner.

Figure 2:
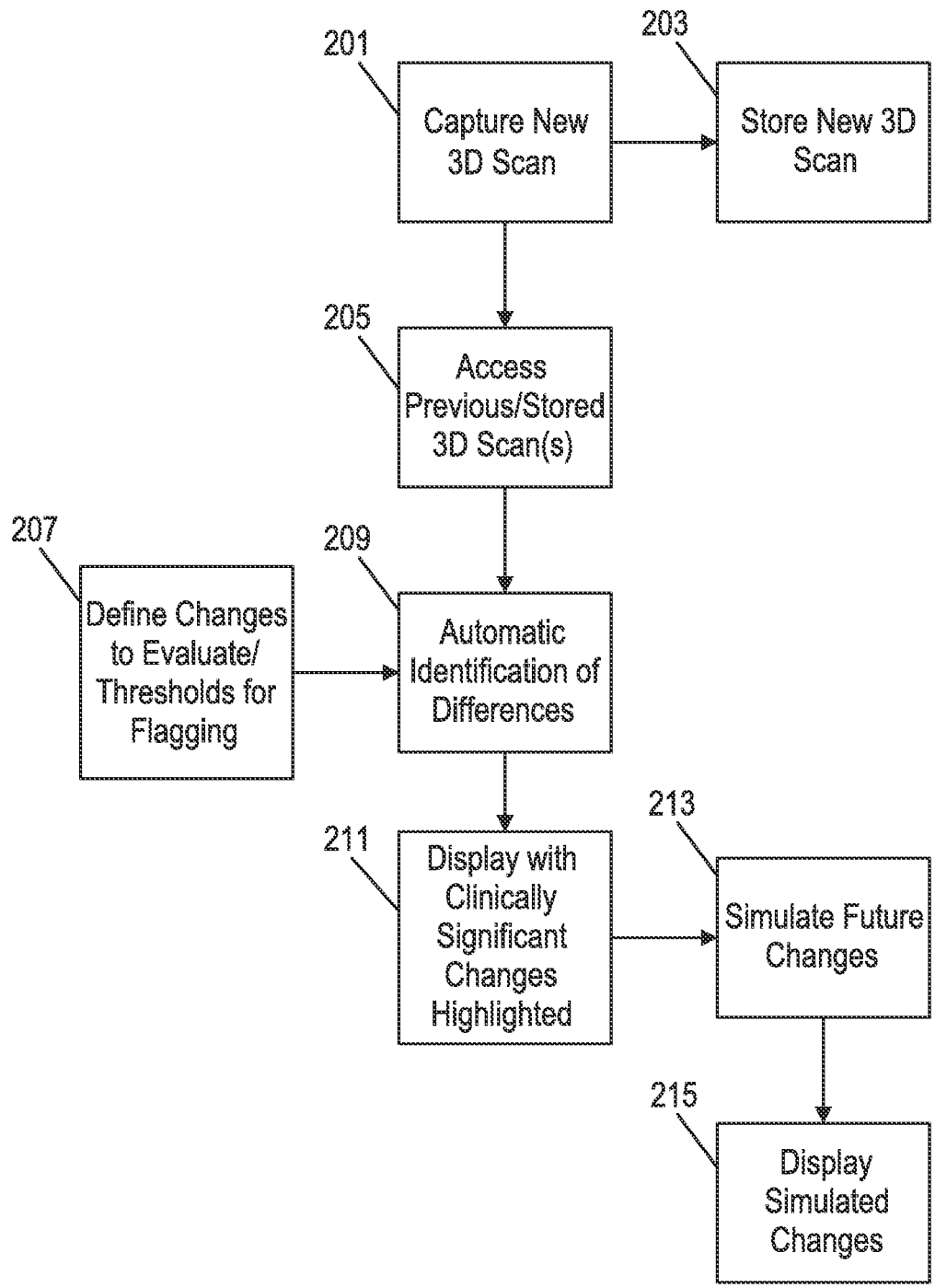
FIG. 2 is a flowchart of a method for monitoring changes in a patient's dentition using the system of FIG. 1.

FIG. 2 illustrates an example of a method for detecting changes in tooth position using the system of FIG. 1. The system 100 receives a new 3D model captured by one of the scanning platforms (step 201). The new 3D model is stored to a memory unit for later access, analysis, and comparison (step 203). A second, previously stored 3D model is accessed from the memory (step 205) and compared to the new 3D model. By comparing two 3D models of from the same patient captured at two different points in time, changes in the patient's dentition or other parts of the oral cavity can be detected. For example, a dentist may capture a new 3D model of a patient at a check-up and compare the new 3D model to a 3D model of the same patient that was captured, generated, and stored at the patient's last check-up.

A user is able to define various analysis criteria to be utilized by the system during the automatic comparison (step 207). For example, a dentist can instruct the system to compare two optically scanned models and two scanned fluorescence models to detect any significant changes in tooth position, gum line position, and chemical structure. The dentist can also define various thresholds that cause the system to flag certain characteristic changes as relevant or clinically significant. For example, the dentist can define a gum-line movement threshold of 2 mm. If the system detects a difference in the position of the gum-line of more than 2 mm between the two digital models, the system will display a notification to the dentist indicating that a clinically-significant change has been detected and prompting the dentist to view the comparison models in further detail. By setting threshold criteria and by automatically flagging clinically-significant changes, the system can more easily make the dentist aware of conditions that should be further explored and evaluated instead of leaving the dentist to detect such changes on his own.

In this way, the system is able to detect clinically-significant changes that could not be detected by visual inspection of a patient's teeth and dental records (i.e., visual comparison of x-rays). As discussed above, a dentist can adjust system settings to define the specific criteria that will indicate what will be considered a "clinically-significant change" and, therefore, will be flagged by the system. However, in some other constructions, the system is pre-programmed based on generally accepted diagnostic theory and other mechanisms to identify what criteria are indicative of a "clinically-significant" change. Therefore, a "clinically-significant" change is one that is defined by the system (either through pre-programming or by user customization) as a change that should be highlighted to a user after the comparison is completed.

Figure 3:
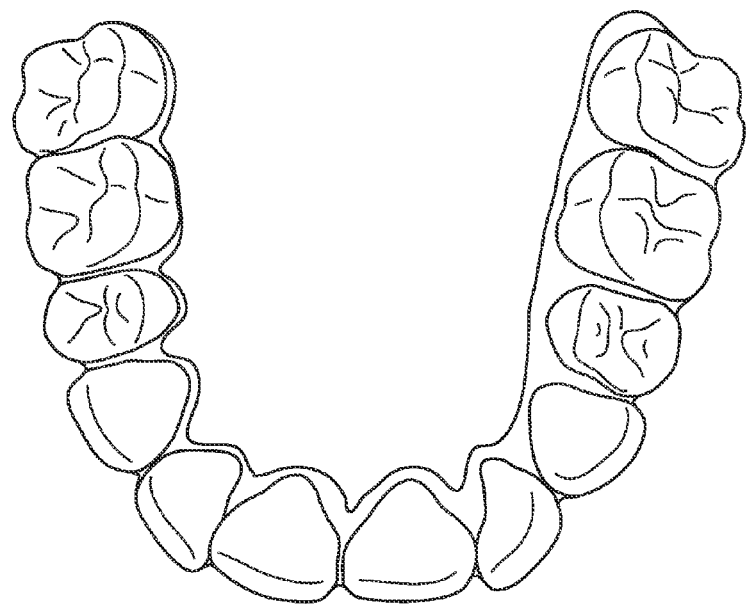
FIG. 3 is an overhead view of a 3D digital rendering of a patient's dentition at a first time.
Figure 4:
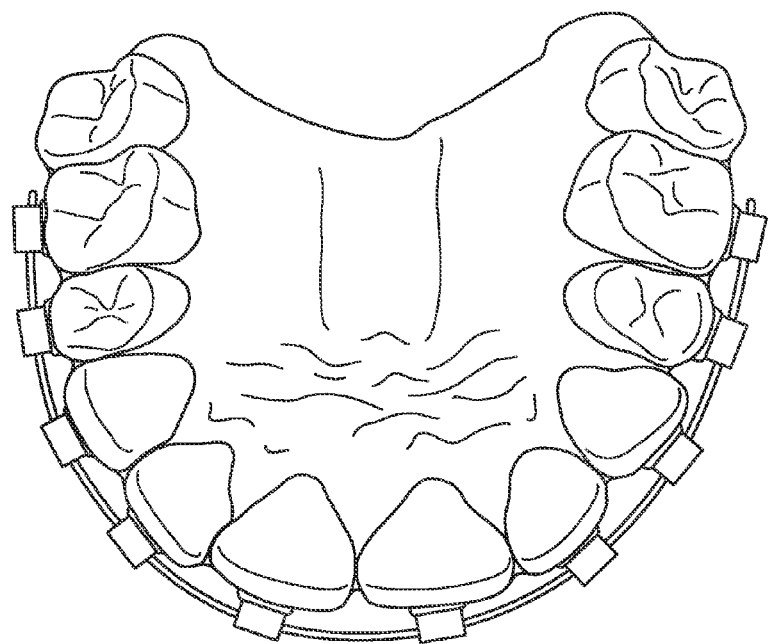
FIG. 4 is an overhead view of a second 3D digital rendering of the patient's dentition from FIG. 3 after treatment with a dental appliance over a period of time.

After the system 100 has compared the 3D digital models and automatically identified differences (step 209), an image is displayed to the user highlighting any clinically-significant changes (211). For example, FIG. 3 shows a first 3D digital model of a patient's upper teeth generated based on an optical surface scan. FIG. 4 shows a second 3D digital model of the same patient's upper teeth after corrective braces have been installed and a period of time has elapsed. It can be difficult to properly characterize or evaluate any changes in tooth position simply by looking at these two digital renderings next to each other. To facilitate the characterization and/or evaluation, the system 100 also generates a composite model based on the data from both the first 3D digital model (FIG. 3) and the second 3D digital model (FIG. 4). This combined model, shown in FIG. 5, more clearly highlights changes in tooth position over time. The patient's left front incisor has moved from a first position 501A to a second position 501B as a result of the corrective treatment implemented by the braces. Similarly, the patient's right front incisor has moved from a first position 503A to a second position 503B since the braces were installed.

Figure 5:
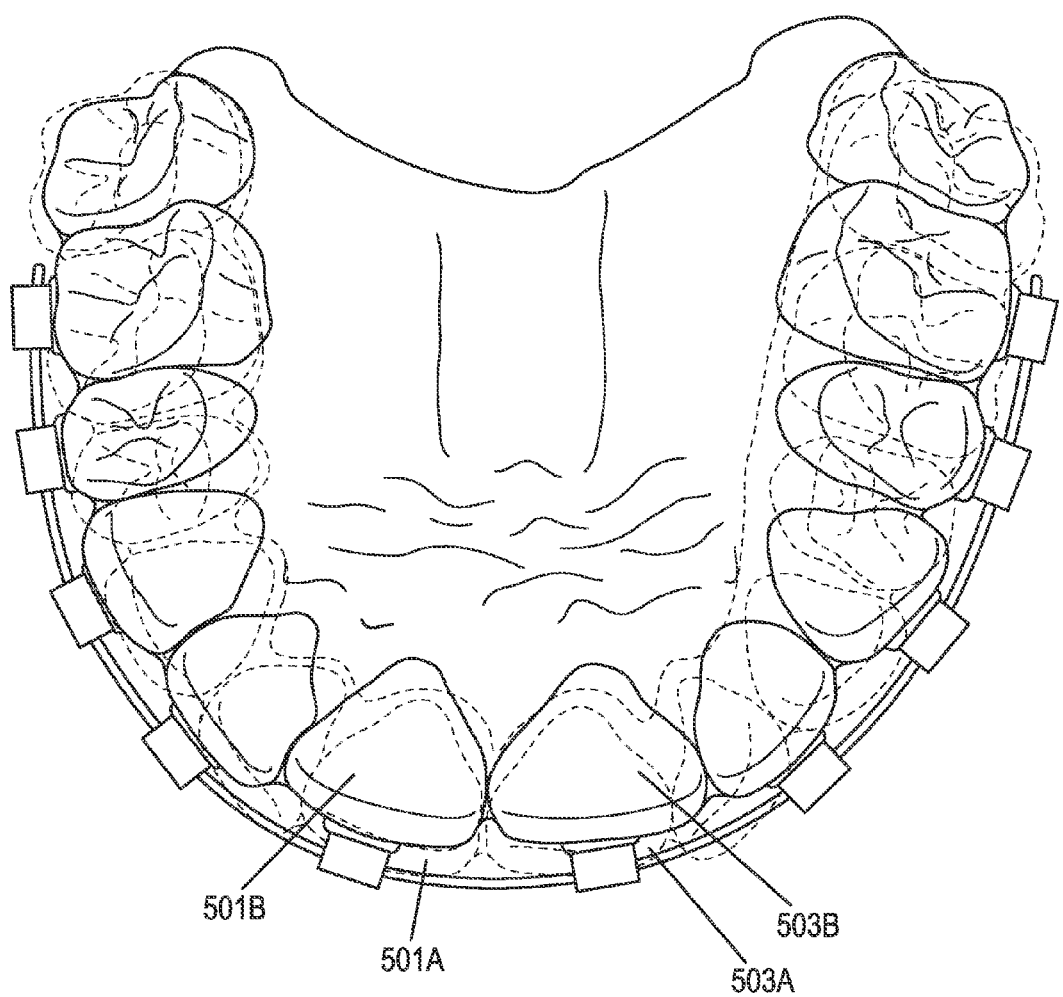
FIG. 5 is a combined 3D digital model demonstrating changes in the teeth position in the digital rendering of FIG. 4 as compared to the digital rendering of FIG. 3.

In addition to showing the overlaid model of FIG. 5, the system allows the user to selectively toggle back-and-forth between the current model (FIG. 4) and the previous model (FIG. 3). The toggling between various image displays (e.g., the overlaid/superimposed models of FIG. 5, the current model of FIG. 4, and the previous model of FIG. 3) can be performed based on user input or can be configured to automatically toggle between various image displays at the defined frequency. The toggling can transition back-and-forth between two images or provide a sequential progression between three or more image displays. Furthermore, in some constructions, the system 100 provides a user interface that allows the user to select a specific view for a number of choices (for example, by an on-screen button or a drop-down menu) and allow the user to transition between various image views without a defined sequence. In still other constructions, the system 100 generates an animation showing the transition from the first position (FIG. 3) to the new, current position (FIG. 4) to visually show the changes in tooth position on an accelerated timeline.

The system is configured to toggle between image displays based on one or more toggle instructions. In some constructions, the toggle instruction is generated in response to a user input. For example, a user can repeatedly select a single button on the user interface to continually cycle through a series of two or more image displays and the system may generate a unique toggle instruction based on the image display that is being shown when the toggle instruction is generated/received. In other constructions, the user interface can include a plurality of buttons each corresponding to a specific image display. In this way, the system generates a unique toggle instruction based on the specific button that is selected by the user. In still other constructions, the toggle instruction is automatically generated by the system processor at a defined frequency to automatically cycle through a series of two or more image displays.

Figure 6A:
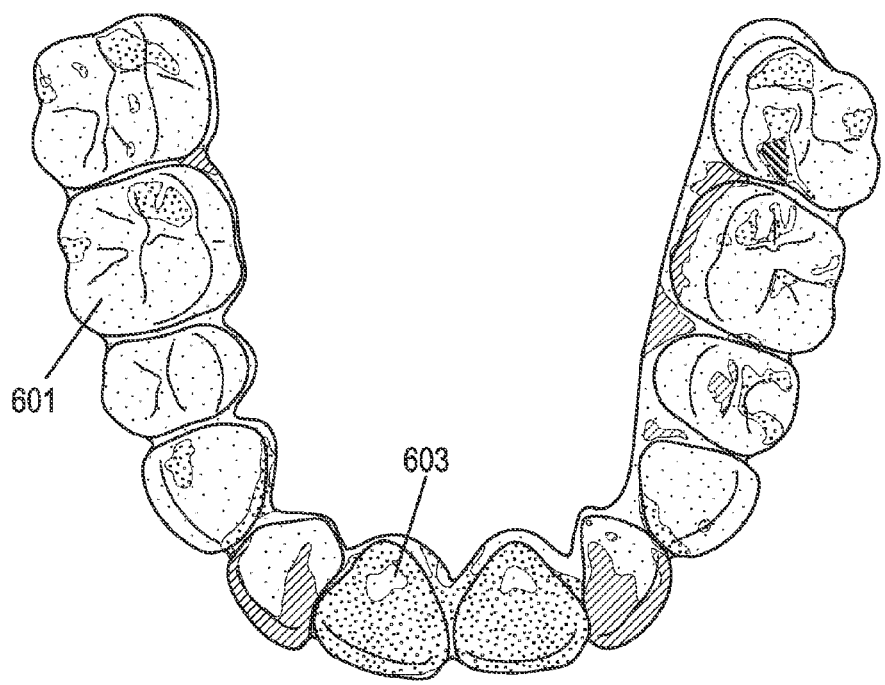
FIG. 6A is an overhead display of a digital rendering of a patient's dentition for quantitatively demonstrating changes in tooth position using color coding.

The system 100 can also show changes quantitatively by displaying numeric data summarizing the movement (e.g., the lateral distance change in mm). Alternatively, the system 100 is equipped to provide a plurality of different viewing mechanisms that can be selected by the user/operator. For example, FIG. 6A shows the second 3D digital rendering (from FIG. 4) with the braces removed. Instead of overlaying the second rendering and the first rendering, the movement in tooth position is quantitatively illustrated by color coding. The molars 601 have undergone relatively little movement since the braces were installed and, therefore, are illustrated in a first color (e.g., green). In contrast, the front incisors have undergone more substantial movement and are, therefore, illustrated in a second, different color (e.g., blue or red).

Figure 6B:
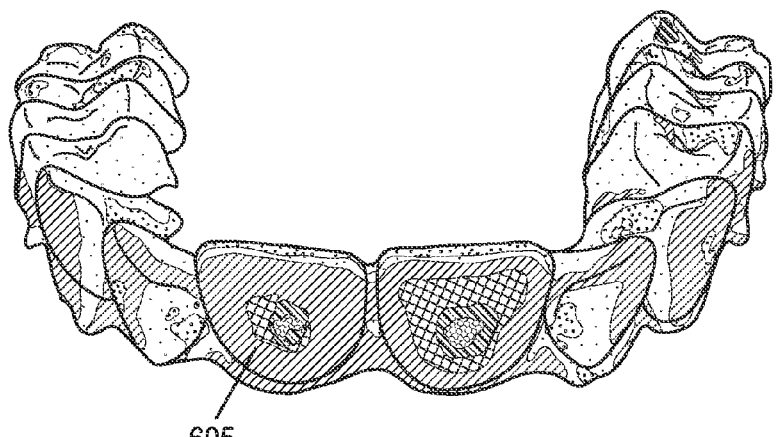
FIG. 6B is a perspective view of the digital rendering of FIG. 6A.

The system 100 also allows the user to manipulate the positioning of the 3D renderings to view different aspects of the patient's oral models. For example, FIG. 6A shows the upper teeth from below. In contrast, FIG. 6B shows the same teeth from a forward perspective. By changing the orientation/perspective of the model rendering, the user is now able to view data indicative of changes in position of the front of the teeth 605. In some constructions, the system 100 provides a plurality of pre-set orientations that the user can select, for example, by either pressing a button on a graphical user interface or selecting from a drop-down menu interface. In other constructions, the user can more freely manipulate the orientation by using the up-down-right-left keys on a keyboard interface or by clicking and dragging on the model using a mouse.

It should be noted that, although FIGS. 3, 4, 5, 6A, and 6B only show changes in the position of a single row of teeth, the system 100 can be used to display other significant data or information, including the data and information discussed above. For example, the system can display a more complete oral scan to show the position of a patient's gum-line and to demonstrate changes in the gum line position over time. Similarly, as also discussed above, the system 100 can display both the upper and lower jaw of the patient (either closed or opened) based on user preference.

In some constructions, the subject matter shown on the display will be determined based on the user's preset preferences (step 207 of FIG. 2) and based on specific significant changes detected and flagged by the system. For example, the system 100 may show only the patient's teeth if it determines that there has been a clinically-significant change in the patient's tooth position, color, or chemistry (based on user defined thresholds/criteria). However, the system 100 may instead show a more complete model that includes both the teeth and the gum line if clinically-significant changes in gum line position are detected.

Returning to FIG. 2, the system 100 also simulates future changes based on previously captured and stored data (step 213) and displays these predicted renderings to the user on the display (step 215). For example, if the system detects a change in a patient's tooth position between a current visit and a previous visit, the system can predict the patient's hypothetical tooth position at a future point in time. Other mechanisms for predicting orthodontic and periodontal changes may be adapted to generate the predictive modeling techniques implemented by the system 100.

Figure 7:
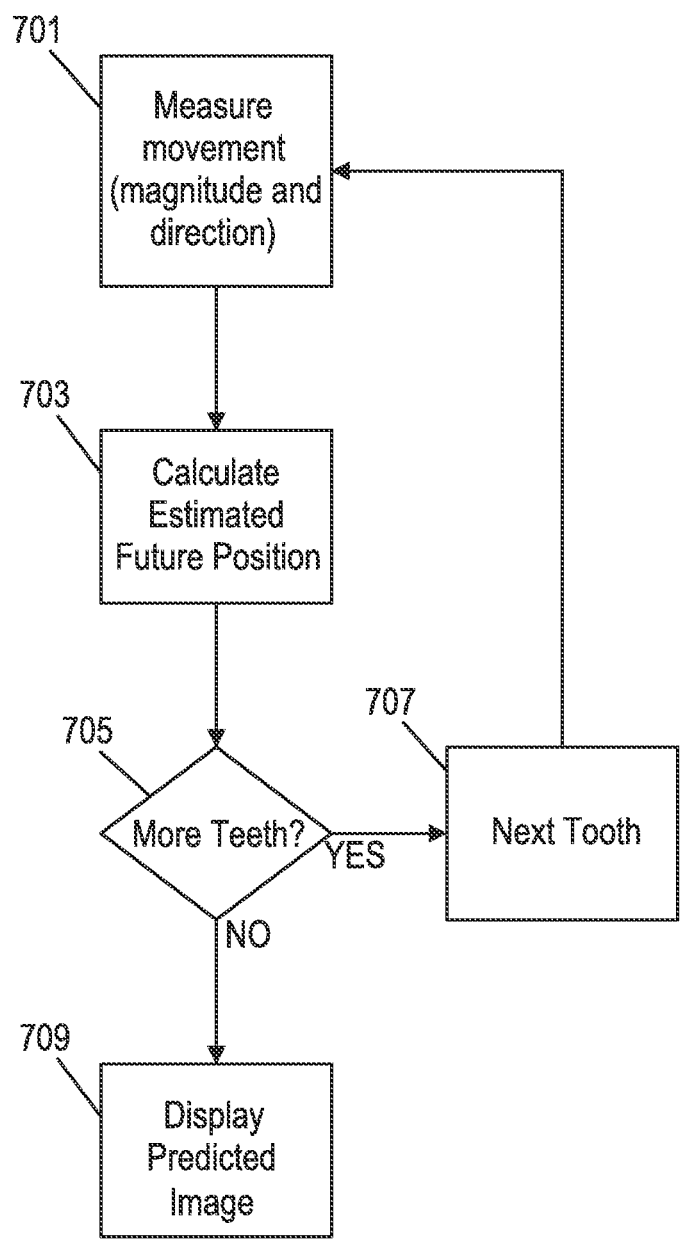
FIG. 7 is a flowchart of a method for generating and displaying a predictive rendering of tooth position using the system of FIG. 1.

FIG. 7 illustrates one example of a method for predicting a future position of a patient's teeth based on previously stored dental models. The system 100 determines a magnitude and direction of change in tooth position over time (step 701) and calculates an extrapolated or otherwise estimated future position of the tooth based on the measured change (step 703). Once a predicted position of a tooth is determined, the system 100 adds the predicted tooth position to a new predicted model rendering of the patient's oral cavity. If more teeth remain to be analyzed (step 705), the system moves to the next tooth (step 707) and continues to predict future tooth positioning on a tooth-by-tooth basis. Once the future position of each of the patient's teeth has been predicted, the system displays the predicted image to the users (e.g., the dentist and the patient).

The estimation of a future position for each individual tooth can be based on predicted linear movement or predicted non-linear movement based on the comparison of two or more 3D digital models for the patient that are stored on the system 100. For example, one predictive model that estimates future tooth position based on linear movement monitors a location of a mid-point of the tooth crown or another point on the tooth volume and measures movement of that single point between two chronologically separated 3D digital models. The system 100 compares two chronologically separated 3D digital models for the same patient and determines a direction of movement (e.g., linear movement or angular movement) and a rate of movement. An estimated future position and orientation of the single tooth is then determined by continuing to move the location of that single point on each individual tooth at the same rate and in the same direction (i.e., an angular or linear direction) relative to a fixed location (e.g., the patient's jaw). A 3D predicted model is then generated based on the estimated future position and orientation of each tooth.

Predictive models that estimate non-linear movement may take into account movements of a single point on a tooth over several chronologically separated models, determine when movement of the tooth is slowing or increasing, and utilize that detected changing rate of movement to estimate a future position of each individual tooth. Furthermore, in some constructions, the system 100 monitors multiple points on each individual tooth to detect changes in yaw, pitch, and roll of the tooth and to utilize those detected changes to estimate a future position of the tooth. Additionally, some predictive modeling techniques account for the fact that the movement of one tooth will affect or be restricted by the movement/location of another, neighboring tooth. Therefore, in some constructions, the predictive modeling techniques analyze movement of individual teeth in parallel and predict how changes in position of one tooth will restrict or expedite movement of other teeth.

As discussed above, some constructions of the system 100 include an external system that stores a series of dental models for a large number of patients. In some constructions, this shared database is implemented as a cloud storage mechanism that is used by the system 100 to provide detailed predictive modeling based on observed changes in other patients. For example, characteristics of a progression of stored models for a first patient can be fitted to a corresponding progression of stored models for one or more other patients who have exhibited similar tooth movement. Future movement of the first patient's teeth can be predicted based on subsequent models from the matched progression of stored models for the one or more other patients. In this way, the system 100 uses a repository of data for many patients to identify a specific real-world example of dental changes that closely match those exhibited by the first patient and to generate a prediction for future tooth movement based on the identified real-world example. As more patients are added to the system and more subsequent 3D models are added to the shared database (or cloud environment), the system 100 becomes self-learning and can provide increasingly accurate predictive modeling.

Although the method of FIG. 7 specifically addresses predicting tooth position, similar progression-based prediction techniques can be used to estimate further regression of a patient's gum line, deterioration of enamel, changes in tooth color, changes in tooth chemistry, etc. Furthermore, observed changes in one dental characteristic can inform the prediction for another. For example, the system 100 may be configured to detect the onset of periodontal disease based on a change in color of a specific tooth. Because periodontal disease may weaken the root and make the tooth more susceptible to movement or loss, the predictive modeling algorithm may apply a significantly greater rate of progression in the visual symptoms associated with periodontal disease (or may even predict that the tooth will fall out) based on the detected change in color.

Cross-modality predictions like these can also be implemented in constructions that utilize the shared database (or cloud environment) for predictive modeling based on other real-world examples. For example, a progression of stored models from another patient can be better fitted to those of a current patient by matching multiple characteristics (e.g., color changes at a similar rate, similar tooth wear, similar gum-line retraction, and similar tooth movement). Some constructions of the cloud-based predictive system also categorize and match patient datasets based on other criteria including, for example, diagnosed diseases, age, ethnicity, and geographic location.

Some constructions of the system 100 may only implement a single predictive modeling technique for all patients. However, in other constructions, the system 100 may select a predictive modeling technique or fine-tune the application of the modeling technique based on identified discriminating characteristic of the patient's dentition/oral cavity. For example, the system 100 may be configured to identify patients with a uniquely narrow dental arch and to apply a specific predictive modeling algorithm that is designed specifically for patients that have a narrow dental arch.

Once a predicted model is generated, the system 100 can display the predicted model in isolation and can also provide a comparison of the predicted model to the current position of the patient's oral structure. For example, the system can overlay the predicted model onto the current 3D digital model of the patient's teeth to visually depict differences in tooth position between the two models (e.g., as shown in FIG. 5). The system 100 can also use the color-coding technique of FIGS. 6A and 6B to quantitatively display tooth movement characteristics.

This predictive modeling can be used by the dentist to demonstrate the predicted effect of certain forms of treatment and the effect of continuing other forms of oral care. For example, if clinically-significant negative changes due to poor oral hygiene are detected in a patient, the predicted modeling can be used by the dentist to demonstrate the effect of continued poor oral hygiene (e.g., "If you don't start brushing and flossing better, this is what your tooth color will look like next year and your gum line will have escaped further by 2 mm."). Similarly, predictive modeling can be used demonstrate the need for corrective orthodontic treatment (e.g., "If we don't do the corrective orthodontic treatment now, your teeth will be in this position in two years. Therefore, it is better to do the treatment now than to wait and perform it later."). Furthermore, the predictive modeling can be used to demonstrate the anticipated effect of dental treatments. For example, a dentist can use the system to compare the patient's current tooth position to the expected tooth position after having corrective braces installed.

The system can also be used by a dentist in preparation for a patient visit. The system can use previously stored model renderings to generate a predicted model of the patient's oral cavity at the time of the upcoming patient visit. The dentist can then inspect the patient's oral cavity virtually before the patient walks in for his appointment. Furthermore, the system can compare the predicted, virtual model of the patient's teeth to an actual model captured during the patient's visit. This comparison will automatically highlight any unexpected changes in the patient's oral cavity due, for example, to improved oral hygiene or newly developed acute oral disease (e.g., oral cancer).

Similarly, the predictive modeling can be used to evaluate the effectiveness of various forms of dental treatment. For example, if corrective braces have been installed on a patient's teeth, the system can be used to generate a predictive model of what the patient's teeth should look like at a scheduled appointment. If the patient's actual tooth position does not appropriately match the predicted tooth position, the dentist can modify the prescribed therapy accordingly (e.g., adjusting the tension in the braces).

As described above, the system can be used to evaluate and predict changes in various aspects of a patient's oral cavity. Although the systems and mechanisms for linear, non-linear, and model-based predictive modeling are discussed in terms of changes in tooth position, similar modeling techniques can be implement to evaluate and predict changes in tooth form, tooth position, tooth color, chemical structure of tooth, position (i.e., retraction) of gum line, shape of soft tissues, and color of soft tissues.

Changes in tooth form can be indicative of tooth wear, decay of enamel, chipping, or loss of restorations. To evaluate changes in tooth form, the system segments the teeth from two digital models taken at different times. In some constructions (e.g., those with models constructed using optical surface scanning), the tooth model is segmented to include only the crown. In other constructions (e.g., when a CT scanning platform is used to generate the 3D model), the segmented teeth can include both the crown and the root. The system then performs a best fit overlay of teeth individually based on features that are least likely to change (e.g., buccal and lingual surfaces). The system then visualizes the differences in shape for each tooth individually as a "heat map" (i.e., quantitative color coding). Alternatively or additionally, the system can perform a best fit overlay of the two scans of an entire arch and may visualize the differences in the overall arch as a "heat map." Changes in the shape of soft tissues can be similarly evaluated and displayed by overlaying the entire arch model or by segmenting other specific portions/anatomical structure of the model. Changes in tooth form can be predicted by linear modeling, non-linear modeling, or fitting models to stored data from other patients as discussed above. For example, in some constructions, the system will monitor changes in height or shape of the dental arch or of individual teeth due to bruxism or wear and may apply the same wear rate to predict a height or shape of the teeth at a future date.

Changes in tooth position in relation to each other can indicate a need for orthodontic treatment and possibly other health conditions that impact tooth position. Changes can also be indicative of the effectiveness of a currently prescribed orthodontic treatment. To evaluate changes in tooth position, the system establishes a common geometry for two or more data sets. In some constructions, this is done by identifying three common points in the data sets. In the case of follow-up orthodontic treatment, the braces on the teeth or points in the oral cavity midline (i.e., palate) can be used as markers for establishing a common geometry between scans. The teeth are again segmented from the model as described above. Furthermore, if bone information is available in the data set (i.e., CT scan models), the models can be aligned using the jaw bone itself. The models are then overlaid and displayed (i.e., FIG. 6). Additionally, changes in tooth position are quantified by comparing the midpoint locations of each crown. This data can be shown numerically or displayed graphically as a "heat map" (i.e., quantitative color coding).

As noted above, changes in tooth color can be indicative of staining, calculus development, or changes in tooth vitality. Changes in color can be evaluated by again segmenting the teeth from the overall model as discussed above. Changes in color can be demonstrated in binary by coloring surfaces on the model where the difference in color between two scans exceeds a threshold. Alternatively, a "heat map" can be used to illustrate a degree of difference in color at each location of each tooth between the two oral scans. A similar comparison/display mechanism is used to demonstrate changes in chemical structure of the teeth; however, although photorealistic optical scan can be used to evaluate color changes, other imaging modalities (e.g., fluorescence imaging) may better demonstrate changes in chemical structure. Changes in the color of soft tissues can be similarly evaluated and displayed. Changes in tooth color can also be predicted using linear, non-linear, and best-fit modeling techniques as described above. For example, in some constructions, the system will monitor a change in color of the tooth (either each individual voxel or an average color of the tooth as a whole) and will predict a future color of the tooth (or specific areas/voxels on the tooth model) by assuming either a linear or non-linear continued change in tooth color (e.g., color, shade, translucency, etc.).

Refraction of the gum line can be indicative of developing periodontal disease or of incorrect brushing technique. To evaluate changes in gum line position, the distance from crown tip to gum line is measured for both a current model and an earlier model at different locations (e.g., buccal and lingual). The differences can be visualized by overlaying one model over the other and by selectively toggling between the two models. Quantitatively, the differences can be shown numerically or by a "heat map" display.

The comparison and evaluation techniques provided by the system are not necessarily limited to the mechanisms described above. For example, three-dimensional models can be generated using x-ray, optical surface scanning, optical photographic imaging (i.e., color surface scanning), or various combinations thereof. Furthermore, fluorescence scanning can be used to monitor and detect oral cancer and lesions. Thermal imaging may be used to identify root infections (i.e., needed root canals), lesions/cancer suspects, changes in blood flow to specific teeth (indicative of tooth vitality), existence/locations of sialoliths, cracks in teeth, sinus problems, effectiveness of local anesthetics, bone/nerve disorders, allergic reactions to treatments/prosthetics, and other periodontal conditions. Other imaging platforms that can be used for comparison include, for example, photography, transillumination, fluorescence, and ultrasound.

Although the examples described above are directed towards comparing data captured over an extended period of time (e.g., different office visits), the system may also be used to evaluate the patient's short-term response to various stimulus. For example, a first scan may represent a tooth in an unloaded state and the second scan shows the tooth when a torque/force is applied to the tooth. A comparison of these two scans will demonstrate how much a particular tooth moves in response to external forces. Similarly, a second scan may be performed after a pressure is applied to (and released from) the patient's gum. Depending on the specific imaging modality used, the comparison can provide information indicative of changes in temperature, geometry, and color in response to the stimulus.

It should also be understood that, although FIG. 1 shows the system 100 directly coupled to various scanning platforms, the processing and comparison techniques described herein are not necessarily performed by a dedicated computer system that is directly coupled to the scanning device. Instead, in some constructions, a single scanner system (i.e, CT scanner 105) can be used to capture data and general 3D models which are then stored to a memory repository. The stored data/models can then be accessed from the common memory by multiple analysis/display systems through a local area network, wide area network, or Internet. As a result, multiple doctors can work with multiple patients from multiple locations at the same time by comparing stored data/models.

Lastly, although many of the examples discussed above include segmenting individual teeth for analysis, the mechanisms and systems described herein can be adapted to perform analysis on the complete, un-segmented arch.

Thus, the invention provides, among other things, a system and method for generating quantitative comparison data, automatically detecting changes, including clinically-significant changes, and predictively modeling expected oral conditions by comparing two or more dental scans of various imaging modalities for the same patient over time. Various features and advantages of the invention are set forth in the following claims.

What is claimed is:

1. A method of evaluating an oral condition, the method comprising:
   comparing a first digital representation of at least a portion of an oral cavity of a first patient to a second digital representation of the portion of the oral cavity of the first patient, the first digital representation being representative of the portion of the oral cavity at a first time and the second digital representation being representative of the portion of the oral cavity at a second time, the second time being subsequent to the first time;
   automatically identifying at least one clinically-significant difference between the first digital representation and the second digital representation;
   determining a magnitude of the at least one clinically-significant difference; and
   displaying the second digital representation in a way that highlights the at least one clinically-significant difference by displaying the second digital representation with an overlaid color-coding indicative of a degree of change of the clinically-significant difference at different locations in the oral cavity,
      wherein displaying the overlaid color-coding includes displaying a first portion of the oral cavity in a first color when the magnitude of the at least one clinically-significant difference exceeds a threshold at the first portion of the oral cavity, and
      wherein displaying the overlaid color-coding includes displaying a second portion of the oral cavity in a second color when the magnitude of the at least one clinically-significant difference does not exceed the threshold at the second portion of the oral cavity.

2. The method of claim 1, wherein the first digital representation includes a first three-dimensional digital model of the portion of the oral cavity of the first patient and the second digital representation includes a second three-dimensional digital model of the portion of the oral cavity of the first patient, and wherein displaying the second digital representation includes displaying the first digital representation overlaid onto the second digital representation.

3. The method of claim 2, wherein the at least one clinically-significant difference includes a change in position of at least one tooth, and wherein displaying the first digital representation overlaid onto the second digital representation highlights a difference in the position of the at least one tooth in the first digital representation and the position of the at least one tooth in the second digital representation.

4. The method of claim 3, wherein the change in position of at least one tooth includes a change in at least one of the group consisting of a pitch change, a yaw change, and a roll change.

5. The method of claim 2, wherein the at least one clinically-significant difference includes a change in a position of a gum line, and wherein displaying the first digital representation overlaid onto the second digital representation highlights a difference in the position of the gum line in the first digital representation and the position of the gum line in the second digital representation.

6. The method of claim 1, wherein the at least one clinically-significant difference includes a change in tooth shape.

7. The method of claim 1, wherein the at least one clinically-significant difference includes a change in position of at least one tooth, further comprising:
   determining a magnitude of position change for each tooth from the first digital representation to the second digital representation; and
   comparing the magnitude of position change to the threshold, and
   wherein displaying the second digital representation with the overlaid color-coding includes
      displaying at least a portion of a first tooth in the first color if the magnitude of position change for the first tooth exceeds the threshold and
      displaying at least a portion of the first tooth in the second color if the magnitude of position change for the first tooth does not exceed the threshold.

8. The method of claim 7, wherein the change in position of at least one tooth includes a change in at least one of the group consisting of a pitch change, a yaw change, and a roll change.

9. The method of claim 1, wherein the at least one clinically-significant difference includes a change in color of at least one tooth, further comprising:
   determining a magnitude of color change for a first location on a surface of the oral cavity from the first digital representation to the second digital representation; and
   comparing the magnitude of color change to the threshold, and
   wherein displaying the second digital representation with the overlaid color-coding includes
      displaying the surface of the oral cavity with the first location shown in the first color if the magnitude of color change for the first tooth exceeds the threshold and
      displaying the surface of the oral cavity with the first location shown in the second color if the magnitude of color change for the first tooth does not exceed the threshold.

10. The method of claim 1, wherein the second digital representation includes
    a three-dimensional representation of a surface of the portion of the oral cavity,
    additional data of a kind different from the three-dimensional representation, and
    information indicating a geometric relation between the three-dimensional representation and the additional data.

11. The method of claim 1, further comprising:
    generating the second digital representation based on data from a scan of the oral cavity of the patient, and
    generating the first digital representation based on data from an earlier scan of the oral cavity of the patient stored on a computer-readable memory.

12. The method of claim 1, further comprising:
    generating the first digital representation based on data from a scan of the oral cavity of the patient, and
    generating the second digital representation by predicting a future state of the portion of the oral cavity.

13. The method of claim 12, further comprising:
    generating a third digital representation based on data from a second, subsequent scan of the oral cavity of the patient, wherein the second subsequent scan is performed at a time corresponding to the predicted future state of the second digital representation;
automatically identifying at least one clinically-significant difference between the second digital representation and the third digital representation; and
displaying the third digital representation in a way that highlights the at least one clinically-significant difference.

14. A method of evaluating an oral condition, the method comprising:
comparing a first digital representation of at least a portion of an oral cavity of a first patient to a second digital representation of the portion of the oral cavity of the first patient, the first digital representation being representative of the portion of the oral cavity at a first time and the second digital representation being representative of the portion of the oral cavity at a second time, the second time being subsequent to the first time;
stimulating a portion of the oral cavity prior to the second time and subsequent to the first time such that the first digital representation represents a condition of the oral cavity before the stimulation and the second digital representation represents the condition of the oral cavity after the stimulation;
automatically identifying at least one clinically-significant difference between the first digital representation and the second digital representation; and
displaying the second digital representation in a way that highlights the at least one clinically-significant difference.

15. A method of evaluating an oral condition, the method comprising:
generating a first digital representation of at least a portion of an oral cavity of a first patient, the first digital representation being representative of the portion of the oral cavity at a first time, the first digital representation being generated by a first imaging modality at the first time;
generating a third digital representation of at least a portion of the oral cavity of the patient by a second imaging modality at the first time, the second imaging modality being different than the first imaging modality;
generating a second digital representation of the portion of the oral cavity of the first patient, the second digital representation being representative of the portion of the oral cavity at a second time, the second time being subsequent to the first time, the second digital representation being generated by the first imaging modality at the second time;
generating a fourth digital representation of at least a portion of the oral cavity of the patient by the second imaging modality at the second time;
comparing the first digital representation of the portion of the oral cavity of the first patient to the second digital representation of the portion of the oral cavity of the first patient;
automatically identifying at least one clinically-significant difference between the first digital representation and the second digital representation;
displaying the second digital representation in a way that highlights the at least one clinically-significant difference;
automatically identifying at least one second clinically-significant difference between the third digital representation and the fourth digital representation; and
displaying the fourth digital representation in a way that highlights the at least one second clinically-significant difference.

16. The method of claim 15, wherein each of the first imaging modality and the second imaging modality are selected from a group consisting of 3D surface scanning, 2D photographic imaging, radiographic imaging, ultrasound imaging, transillumination, optical coherence tomography, terahertz imaging, infrared reflectance imaging, thermal imaging, and fluorescence imaging.

17. The method of claim 1, further comprising:
receiving a first set of optical surface scan data at the first time;
generating the first digital representation as a first three-dimensional surface model of at least a portion of the oral cavity of the first patient based on the first set of optical surface scan data;
receiving a first set of x-ray data at the first time;
generating a first three-dimensional x-ray model of at least a portion of the oral cavity of the first patient based on the first set of x-ray data;
receiving a second set of optical surface scan data at the second time;
generating the second digital representation as a second three-dimensional surface model of at least a portion of the oral cavity of the first patient based on the second set of optical surface scan data;
receiving a second set of x-ray data at the second time;
generating a second three-dimensional x-ray model of at least a portion of the oral cavity of the first patient based on the second set of x-ray data; and
comparing the first three-dimensional x-ray model to the second three-dimensional x-ray model;
automatically identifying an additional clinically-significant difference between the first three-dimensional x-ray model and the second three-dimensional x-ray model; and
displaying the second three-dimensional x-ray model in a way that highlights the additional clinically-significant difference.

18. The method of claim 1, further comprising:
receiving a first set of optical surface scan data at the first time;
receiving a first set of photographic image data at the first time;
generating the first digital representation as a first three-dimensional surface model of at least a portion of the oral cavity of the first patient based on the first set of optical surface scan data and overlaying the first set of photographic image data onto the first three-dimensional surface model to create a first photorealistic three-dimensional surface model;
receiving a second set of optical surface scan data at the second time;
receiving a second set of photographic image data at the second time; and
generating the second digital representation as a second three-dimensional surface model of at least a portion of the oral cavity of the first patient based on the second set of optical surface scan data and overlaying the second set of photographic image data onto the second three-dimensional surface model to create a second photorealistic three-dimensional surface model.

19. The method of claim 1, further comprising:
receiving a first toggle instruction; and
changing from a first display of the second digital representation to a second display of the second digital representation in response to the first toggle instruction.

20. A method of evaluating an oral condition, the method comprising:
comparing a first digital representation of at least a portion of an oral cavity of a first patient to a second digital representation of the portion of the oral cavity of the first patient, the first digital representation being representative of the portion of the oral cavity at a first time and the second digital representation being representative of the portion of the oral cavity at a second time, the second time being subsequent to the first time;
automatically identifying at least one clinically-significant difference between the first digital representation and the second digital representation;
displaying the second digital representation in a way that highlights the at least one clinically-significant difference;
receiving a first toggle instruction; and
changing from a first display of the second digital representation to a second display of the second digital representation in response to the first toggle instruction, wherein the second digital representation includes a first three-dimensional digital model of the portion of the oral cavity of the first patient and the second digital representation includes a second three-dimensional digital model of the portion of the oral cavity of the first patient, wherein displaying the second digital representation includes displaying the first digital representation overlaid onto the second digital representation, and wherein changing from the first display of the second digital representation to a second display of the second digital representation includes removing the overlaid image from the display and displaying an overlaid color-coding on the second digital representation indicative of a degree of change of the clinically-significant difference at different locations in the oral cavity.

21. The method of claim 19, wherein the second display of the second digital representation is an unaltered three-dimensional display of the second digital representation.

22. The method of claim 21, further comprising:
receiving a second toggle instruction;
changing from the display of the unaltered three-dimensional display of the second digital representation to an unaltered three-dimensional display of the first digital representation in response to the second toggle instruction;
receiving a third toggle instruction; and
changing from the unaltered three-dimensional display of the first digital representation to the unaltered three-dimensional display of the second digital representation in response to the third toggle instruction.

23. A method of evaluating a dental condition, the method comprising:
comparing a first digital representation of at least a portion of an oral cavity of a first patient to a second digital representation of the portion of the oral cavity of the first patient, the first digital representation being representative of the portion of the oral cavity at a first time and the second digital representation being representative of the portion of the oral cavity at a second time, the second time being subsequent to the first time;
automatically identifying at least one clinically-significant difference between the first digital representation and the second digital representation;
determining a magnitude of the at least one clinically-significant difference; and
displaying the first digital representation in a way that highlights the at least one clinically-significant difference by displaying the first digital representation with an overlaid color-coding indicative of a degree of change of the clinically-significant difference at different locations in the oral cavity,
wherein displaying the overlaid color-coding includes displaying a first portion of the oral cavity in a first color when the magnitude of the at least one clinically significant difference exceeds a threshold at the first portion of the oral cavity, and
wherein displaying the overlaid color-coding includes displaying a second portion of the oral cavity in a second color when the magnitude of the at least one clinically-significant difference does not exceed the threshold at the second portion of the oral cavity.

* * * * *